United States Patent
Star-Lack et al.

(10) Patent No.: US 7,860,341 B2
(45) Date of Patent: Dec. 28, 2010

(54) SYSTEM AND METHOD FOR CORRECTING FOR RING ARTIFACTS IN AN IMAGE

(75) Inventors: Josh Star-Lack, Palo Alto, CA (US); Hassan Mostafavi, Los Altos, CA (US); John Pavkovich, Palo Alto, CA (US)

(73) Assignee: Varian Medical Systems, Inc., Palo Alto, CA (US)

(*) Notice: Subject to any disclaimer, the term of this patent is extended or adjusted under 35 U.S.C. 154(b) by 263 days.

(21) Appl. No.: 11/490,690

(22) Filed: Jul. 21, 2006

(65) Prior Publication Data
US 2008/0019607 A1 Jan. 24, 2008

(51) Int. Cl.
*G06K 9/40* (2006.01)
*G06K 9/00* (2006.01)

(52) U.S. Cl. ............... 382/275; 382/131
(58) Field of Classification Search .......... 382/131, 382/275
See application file for complete search history.

(56) References Cited

U.S. PATENT DOCUMENTS

| | | | |
|---|---|---|---|
| 4,670,840 A | 6/1987 | Freundlich | |
| 5,533,081 A | 7/1996 | Hsieh | |
| 5,745,542 A | 4/1998 | Gordon et al. | |
| 5,815,606 A * | 9/1998 | Baker et al. | 382/237 |
| 5,841,828 A | 11/1998 | Gordon et al. | |
| 5,937,102 A * | 8/1999 | Jin | 382/276 |
| 6,044,125 A | 3/2000 | Flohr et al. | |
| 6,047,039 A | 4/2000 | Flohr | |
| 6,115,445 A * | 9/2000 | Lai | 378/4 |
| 6,430,253 B1 | 8/2002 | Oikawa | |
| 6,888,919 B2 * | 5/2005 | Graf | 378/65 |

(Continued)

FOREIGN PATENT DOCUMENTS

DE   31 07 170 A1   2/1981

(Continued)

OTHER PUBLICATIONS

Huang et al., "A Fast Two-Dimensional Median Filtering Algorithm", Feb. 1979, IEEE Transactions on Acoustics, Speech, and Signal Processing, vol. ASSP-27, No. 1, 13-18.*

(Continued)

*Primary Examiner*—Vikkram Bali
*Assistant Examiner*—Katrina Fujita
(74) *Attorney, Agent, or Firm*—Brandon N. Sklar, Esq.; Kaye Scholer LLP

(57) ABSTRACT

In one example of an embodiment of the invention, a method to correct for ring artifacts in an image is disclosed. A first Cartesian image is reconstructed based on data received from an imaging device, and the first Cartesian image is transformed into a first polar image. A first low-pass filter is applied to the first polar image, in the radial dimension, to form a second polar image, and the second polar image is subtracted from the first polar image to generate a third polar image. A second low-pass filter is applied to the third polar image, in an angular dimension, to form a fourth polar image, and the fourth polar image is transformed to Cartesian coordinates to form a second Cartesian image. The first Cartesian image is corrected based, at least in part, on the second Cartesian image.

55 Claims, 15 Drawing Sheets

U.S. PATENT DOCUMENTS

| | | | |
|---|---|---|---|
| 7,391,927 B2* | 6/2008 | Stierstorfer | 382/275 |
| 2004/0068169 A1 | 4/2004 | Mansfield et al. | |
| 2004/0109532 A1 | 6/2004 | Ford et al. | |
| 2005/0271299 A1* | 12/2005 | Ajito et al. | 382/293 |
| 2006/0056579 A1 | 3/2006 | Stierstorfer | |
| 2006/0159363 A1* | 7/2006 | Van De Haar et al. | 382/274 |

FOREIGN PATENT DOCUMENTS

| | | |
|---|---|---|
| EP | 0 769 878 A2 | 4/1997 |
| WO | WO 98/05003 | 2/1998 |

OTHER PUBLICATIONS

Euclid Seeram, Computed Tomography, 2001, pp. 194-195, W.B. Sanders Co., Philadelphia.

Sijbers, J. and Postnov, A., "Reduction of Ring Artifacts in High Resolution Micro-CT Reconstructions," Physics in Medicine and Biology, Jul. 21, 2004, pp. 247-253, vol. 49(14).

M. Zellerhoff et al., Low Contrast 3D-Reconstruction from C-arm Data, Medical Imaging 2005: Physics of Medical Imaging, 2005, pp. 646-655, Proceedings of SPIE vol. 5745, Bellingham, WA.

McGraw-Hill Dictionary of Scientific and Technical Terms, 2003, pp. 336, Sixth Edition, The McGraw-Hill Companies, Inc., USA.

Maria Axelsson et al; "Reduction of Ring Artifacts in High Resolution X-Ray Microtomography Images", Pattern Recognition: 28th DAGM Symposium, Sep. 12-14, 2006, Berlin, Germany.

Richard A. Ketcham; "New algorithms for ring artifacts removal"; Developments in X-Ray Tomography V, Proc. SPIE, vol. 6318, Sections 4-5 , Aug. 2006 (2006-2008).

* cited by examiner

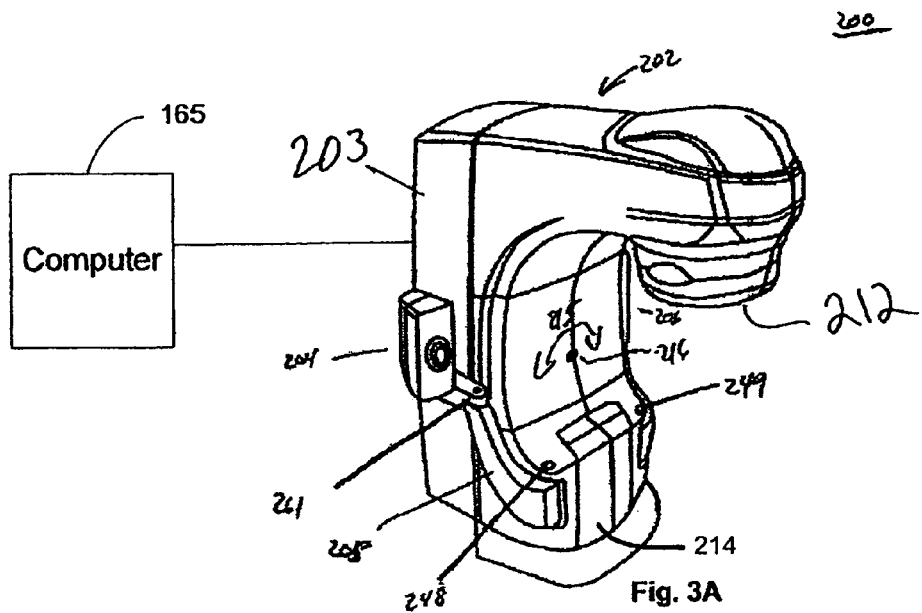
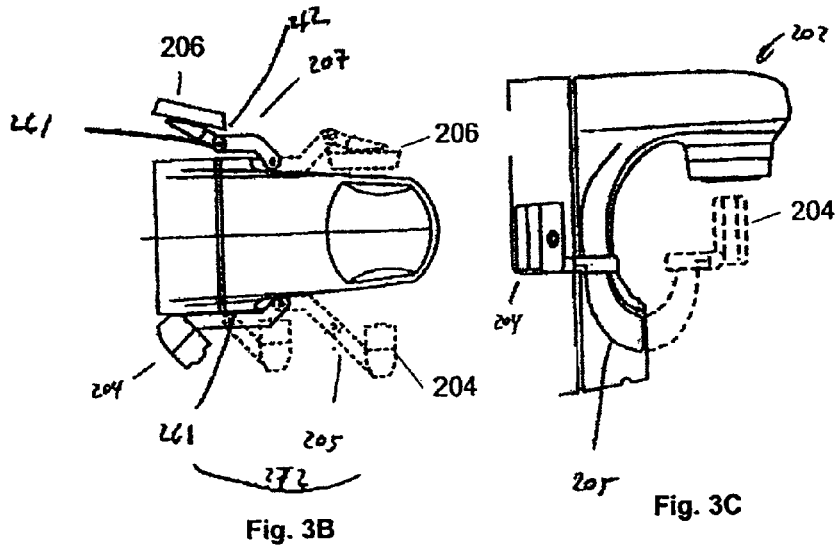
Fig. 3A
Fig. 3B
Fig. 3C

SYSTEM AND METHOD FOR CORRECTING FOR RING ARTIFACTS IN AN IMAGE

FIELD OF THE INVENTION

This invention relates generally to a system and method for reducing artifacts in image data. More particularly, this invention relates to a system and method for identifying and mitigating ring artifacts in image data obtained by computed tomography (CT).

BACKGROUND OF THE INVENTION

Computed tomography ("CT") scanning enables a doctor to obtain detailed images of a patient's internal organs and tissues. CT scanning is used in a variety of medical fields, such as in radiology, cardiology and oncology, to diagnosis conditions and diseases, as well as to plan radiation treatments, for example. CT scanning has also been used in other fields to identify defects in machinery, to perform baggage inspections at airports, and to analyze the internal anatomy of preserved Egyptian mummies, for example.

To obtain a CT image, a portion of a patient or other such target is irradiated by X-ray radiation at a sufficient number of angles to enable CT image reconstruction, as is known in the art. One or more detectors are positioned or are positionable at the plurality of angles, to detect radiation transmitted through the target. The detectors convert the detected X-ray beam into electrical signals (analog signals) that are subsequently converted into digital data for input into a computer. The computer receives the digital data and processes it to reconstruct CT images for analysis.

In accordance with one common type of CT acquisition geometry, referred to as "third generation" CT, an X-ray source, such as an X-ray tube or linear accelerator, and a detector facing the source, are rotated together around a patient or other such target. FIG. 1 is a schematic representation of a front view of a third generation CT system 100 showing a source 102, a detector 104, and a patient 106 lying on a support 108, such as a bench or platform, for example. In this example, the source 102 and detector 104 are simultaneously moved around the patient 106, here in the clockwise direction, as shown by the arrows A. The source 102 and detector 104 may be supported and moved by a rotatable, circular gantry (not shown), as is known in the art. The source 102 and the detector 104 may be supported by a rotatable C-arm, as well, as shown in U.S. Patent Publication No. 2004/0068169 ("the '169 Publication"), which was filed on Oct. 5, 2002 bearing U.S. application Ser. No. 10/264,630, was published on Apr. 8, 2004, was filed on Oct. 5, 2002, and is incorporated by reference herein. The radiation emitted by the source 102 may be collimated into a fan beam or a cone beam. If a fan beam is used, the detectors 104 may comprise one-dimensional detector arrays. If a cone beam is used, the detectors 104 may comprise two dimensional detector arrays. Fan beam and cone beam reconstruction algorithms are known in the art. Ring artifacts may also appear in images generated by CT systems in which the target is rotated. In such systems, the target may be moved vertically or the source and the detector may be moved vertically. Such systems may be used to examine objects, such as cargo containers, for contraband, for example, as described in U.S. patent application Ser. No. 10/310,060, which was filed on Dec. 4, 2002, was published on Jun. 10, 2004 bearing Publication No. 2004/0109532, is assigned to the assignee of the present invention, and is incorporated by reference herein. Such systems may also be used to examine manufactured products for defects, for example.

One problem with third generation CT scanning is the occasional appearance of circular or elliptical ring artifacts in the output image. An example of a CT image with circular, ring artifacts is shown in FIG. 2. Ring artifacts may be caused by one or more faulty detectors that produce varying signal outputs. More specifically, during the rotation of the X-ray source and detector, the rays measured by a given detector are tangent to a circle. If a detector or detector element has a slight offset or gain instability, a circular artifact can appear in the output image due to rotation of that detector around the patient. In addition, mechanical instabilities of the rotatable gantry can produce elliptical rather than circular artifacts. Physical characteristics of the imaging apparatus and/or detector can also cause variable intensity and/or partial ring artifacts (semi-circular, for example). Artifacts can degrade image quality and affect the perceptibility of detail, which can cause serious problems for doctors, for example, who need to provide diagnosis and/or identify a target for treatment based on the output image.

One way to correct for ring artifacts in third generation CT scanners is to locate and recalibrate or replace the faulty detectors. Alternatively, algorithms, such as balancing algorithms, have been used to mitigate ring artifacts. *Computed Tomography*, Euclid Seeram, W.B. Sanders Co., 2nd Edition (2001), pp. 194-195. Examples of algorithms used to mitigate ring artifacts are described in U.S. Pat. No. 4,670,840, U.S. Pat. No. 6,115,445, U.S. Pat. No. 5,533,081, and U.S. Pat. No. 5,745,542.

Software algorithms that correct for ring artifacts are generally complex and must be performed with large amounts of data. This can delay reconstruction/generation of corrected images. During radiotherapy, for example, it is often necessary to obtain images as soon as possible.

An example of a correction algorithm is also described, in Sijbers, J., Postnov, A., "Reduction of ring artifacts in high resolution micro-CT reconstructions," Phys. Med. Biol. 49(14); N247-53, Jul. 21, 2004, ("Sijbers"). Sijbers first transforms an input image in Cartesian coordinates into polar coordinates. Using a sliding window, a set of homogenous rows are identified in the polar image and an artifact template is generated based on the rows. The artifact template is subtracted from the polar image, and the resulting image is transformed back into Cartesian coordinates. It has been found that the quality of such a constant intensity ring correction is not always sufficient and the execution time may be prohibitively long.

Another example of a correction algorithm is described by M. Zellerhoff et al., in "Low Contrast 3D-reconstruction from C-arm data," Medical Imaging 2005: Physics of Medical Imaging, Proceedings of SPIE Vol. 5745 (SPFE, Bellingham, Wash., 2005). First, a "reduced image" of a reconstructed image, containing only pixels associated with soft tissue, is generated. Circular structures in the image are removed by applying a median filter in the radial direction. The difference between this filtered image and the "reduced image" is generated and used as an initial ring image. A two-step smoothing in the circular direction is then performed to eliminate noise and non-circular structures. The resulting final ring image contains only the ring artifacts. The final ring image is subtracted from the original reconstructed image to obtain a corrected image. Zellerhoff states that: "for a better performance the radial and circular filtering steps are implemented using a Cartesian grid. In this case, no coordinate transformation before or after the correction is necessary." (Id. at p. 652).

SUMMARY OF THE INVENTION

Methods and systems are provided herein to correct for various types of ring artifacts, including circular artifacts, partial ring artifacts, elliptical artifacts, and variable intensity artifacts.

In one example of an embodiment of the invention, a method to correct for ring artifacts in an image is disclosed, comprising reconstructing a first Cartesian image based on data received from an imaging device, in Cartesian coordinates, and transforming the first Cartesian image into a first polar image in polar coordinates. The method further comprises applying a first low-pass filter to the first polar image, in the radial dimension, to form a second polar image, and subtracting the second polar image from the first polar image to form a third polar image. The method additionally comprises applying a second low-pass filter to the third polar image, in the angular dimension, to form a fourth polar image, and transforming the fourth polar image to Cartesian coordinates to form a second Cartesian image. The first Cartesian image is corrected based, at least in part, on the second Cartesian image.

In one example, the first Cartesian image is corrected by subtracting the second Cartesian image from the first Cartesian image. The first low-pass filter may be applied by applying a median filter in the radial dimension, for example. Applying the median filter may comprise determining local median values with a sliding window technique in the radial dimension. A histogram may be used to determine local median values. The second low-pass filter may be performed by calculating median intensity values for sets of pixels at constant angular values and replacing selected values in the preliminary ring image with median intensity values. Applying the second low-pass filter may further include applying circular convolution in the angular dimension.

In another embodiment of the invention, a method to correct for ring artifacts in an image is disclosed, comprising converting a Cartesian image in Cartesian coordinates into a polar image in polar coordinates, identifying polar ling artifacts in the polar image, and filtering the identified polar ring artifacts. The method also comprises obtaining a corrected Cartesian image based, at least in part, on the filtered polar ring artifacts. The corrected Cartesian image may be obtained by converting the filtered polar ring artifacts into Cartesian ring artifacts, and subtracting the Cartesian ring artifacts from the Cartesian image. Alternatively, the corrected Cartesian image may be obtained by subtracting the polar ring artifacts from the polar image, and then converting the polar image to Cartesian coordinates.

In another embodiment of the invention, a computed tomography system is disclosed comprising a support to support a target, at least one radiation source positioned to irradiate the target, and at least one detector positioned to detect radiation interacting with the target. A processor is coupled to the detector. The processor is configured to correct for ring artifacts by converting a Cartesian image in Cartesian coordinates into a polar image in polar coordinates, identifying polar ring artifacts in the polar image, filtering the identified polar ring artifacts, and obtaining a corrected Cartesian image based, at least in part, on the filtered polar ring artifacts.

The system may further comprise a second support that is rotatable around an axis, to support a source and a detector. The support may comprise a gantry. The source and the detector may be coupled to the rotatable gantry. The support may further comprise a C-arm comprising first and second arms, coupled to the rotatable gantry, each arm to support a source and a detector, respectively. The system may also comprise a radiotherapy system.

Alternatively, the first support supporting the target may be rotatable around an axis and the source, the detector, and/or the support may be movable in a direction parallel to the axis, such as vertically, for example.

In another embodiment of the invention, a method of conducting computed tomography is disclosed comprising irradiating a target, detecting radiation interacting with the target, and reconstructing an image in Cartesian coordinates based, at least in part, on radiation detected by the detector. The method further comprises converting the image in Cartesian coordinates into polar coordinates to form a polar image, identifying ring artifacts in the polar image, filtering the identified ring artifacts in polar coordinates, and obtaining a corrected Cartesian image based, at least in part, on the filtered polar ring artifacts.

In another embodiment of the invention, a system to correct for ring artifacts in an image is disclosed comprising a memory to store data and a processor coupled to the memory. The processor is configured to convert a Cartesian image into a polar image, identify polar ring artifacts in the polar image, filter the identified polar ring artifacts and obtain a corrected Cartesian image based, at least in part, on the filtered polar ring artifacts.

In another embodiment of the invention, machine readable code stored on a storage medium for use in an image processing system is disclosed, to correct ring artifacts in an image. The code comprises instructions to convert a Cartesian image into a polar image, identify polar ring artifacts in the polar image, filter the identified polar ring artifacts, and obtain a corrected Cartesian image based, at least in part, on the filtered polar ring artifacts.

BRIEF DESCRIPTION OF THE DRAWINGS

FIGS. 3A-3C show external views of an example of a radiotherapy clinical treatment machine, in accordance with an embodiment of the invention;

DETAILED DESCRIPTION OF THE PREFERRED EMBODIMENTS

In one example of an embodiment of the invention, an image generated by third generation CT scanning is examined and processed by a computer to correct for ring artifacts in the image. In this example, raw CT data is reconstructed into an image in Cartesian coordinates. The Cartesian image is transformed into an image in polar coordinates. Polar ring artifacts are identified in the polar image, and the identified polar ring artifacts are filtered. The Cartesian image is then corrected based, at least in part, on the filtered polar ring artifacts. To filter the polar ring artifacts, in one example, a row-based low-pass filter is applied to the polar image to generate a local median value matrix, which is subtracted from the polar image to generate a polar image of the ring artifacts. A column-based low-pass filter is then applied to the polar image. In one example, the row and column filtered polar image, which is in polar coordinates, is transformed into Cartesian coordinates, and subtracted from the first Cartesian image to generate a corrected image, with reduced or no ring artifacts. The row and column filtered polar image may also be subtracted from the first polar image and the resulting image then converted into Cartesian coordinates. As used herein, the term "image" refers to reconstructed data, whether stored in memory in any convenient format or displayed as a two-dimensional image on a display screen comprising a plurality of pixels, or as a printed image, for example.

Figure 1:
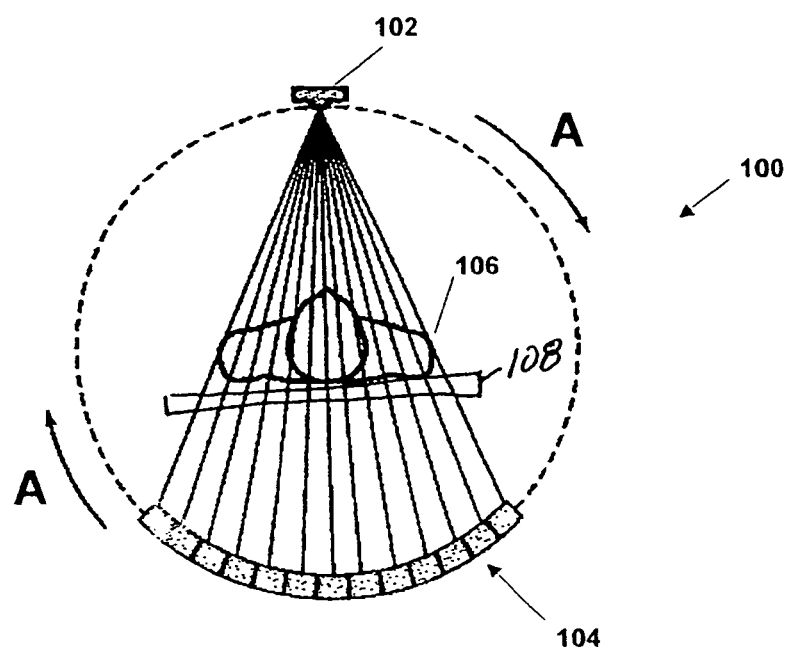
FIG. 1 is a schematic representation of a front view of a third generation CT scanning system, as is known in the art.

FIGS. 3A-3C show various views of an example of a radiotherapy clinical imaging/treatment machine 200 having a third generation configuration (as shown schematically in FIG. 1), to image a selected volume of a patient (such as a tumor), and to conduct radiation therapy using a radiotherapy device to irradiate a selected target volume. While not shown in these views, a patient may be supported in proximity to the machine 200 by a support, such as a bench or a platform, as is known in the art and is shown schematically in FIG. 1. The radiotherapy clinical treatment machine 200 is described in further detail in U.S. Patent Publication No. 2004/0068169 (the "'169 Publication"), which was filed on Oct. 5, 2002 bearing U.S. application Ser. No. 10/264,630, was published on Apr. 8, 2004, is assigned to the assignee of the present invention, and is incorporated and by reference herein. The machine 200 is available from Varian Medical Systems, Palo Alto, Calif., under the tradename Trilogy™ System.

The machine 200 has a rotatable gantry 202 that is rotated by a drive stand 203. The gantry 202 supports and rotates articulable robotic arms 205, 207 about a patient (not shown). The rotatable gantry 202 is pivotably attached to a drive stand 203 of the machine 200. One or more imaging sources 204 and one or more imaging detectors 206 are supported by the articulable robotic arms, 205, 207 to conduct CT scanning of the patient. The source 204 may emit a fan beam or a cone beam of X-ray radiation having energies in the KeV range, for example. The gantry 202 is capable of 360-degree rotation 215 about a centerline 216, to move the arms 205, 207, and thereby the source 204 and the detector 206, around a patient, in a third generation CT scanning configuration. The arms 205, 207 swing laterally to/from a storing position from/to an imaging position, to provide variable positioning and clearance for imaging and radiation treatment applications.

FIG. 3A is a perspective view of the machine 200. The articulating robotic arms 205, 207 are each attached to pivot points 248 and 249, respectively, at the base of the rotatable gantry 202, for extension and retraction. The opposite end of the arm 205 is pivotally attached to the imaging source 204. The opposite end of the arm 207 is pivotally attached to the imaging detector 206. For imaging, the robotic arms 205 and 207 swing outward into an adjustable imaging position along a defined trajectory 272, as shown in phantom FIG. 3B. In one example, the detector 206 may comprise an amorphous silicon flat panel detector, such as a Paxscan®, available from Varian Medical Systems, Inc., Palo Alto, Calif., for example. A high energy radiation source 212 (emitting radiation having energies in the MeV range) and another detector 214 (shown stowed within the gantry 202 in FIG. 3A) are also provided to conduct radiation treatment and to image.

FIG. 3B and FIG. 3C show arms 205, 207 folded against the rotatable gantry 202 to provide more clearance. FIG. 3B is a top view and FIG. 3C is a side view of the machine 200, showing the swinging motion of robotic arms 205, 207 to position the radiation source 204 and detector 206 for positioning and clearance and for imaging (shown in phantom). Each arm 205, 207 also includes respective pivot points 261 and 262 that add to the maneuverability and positioning of the arm. FIG. 3C also shows that each arm 205 and 207 may be curved to conform to the shape of the gantry 202, to maximize patient clearance.

As shown in FIG. 3A, the machine 200 is connected to a computer 165 programmed to reconstruct images, correct for ring artifacts in accordance with an embodiment of the invention, and to control the operation of the machine. While in this example one computer 165 is shown, the system of FIGS. 3A-C may comprise multiple computers, some or all of which being dedicated to different functions. The image detector 206 detects radiation that has passed through a selected volume and, in response, generates digital image data, which is transmitted to the computer 165 for image reconstruction and ring artifact correction. The computer may be a general purpose computer or a special purpose computer. The radiotherapy clinical treatment machine 200 may be directly connected to the computer 165, or may be connected to the computer 165 via a network. While being described in connection with the imaging/radiotherapy machine 200, embodiments of the invention may be used with any third generation CT scanning apparatus. Embodiments of the invention may also be used with CT systems in which the target is rotated, as described below with respect to FIG. 14, or other CT or scanning configurations where ring artifacts are present.

After a target volume definition has been provided by the imaging radiation source 204, the imaging detector 206 and the imaging radiation source 204 may be retracted for clearance via their respective robotic arms. The gantry 202 can be rotated into position to administer a treatment beam from the radiation source 212, based on the target volume definition.

Figure 4:
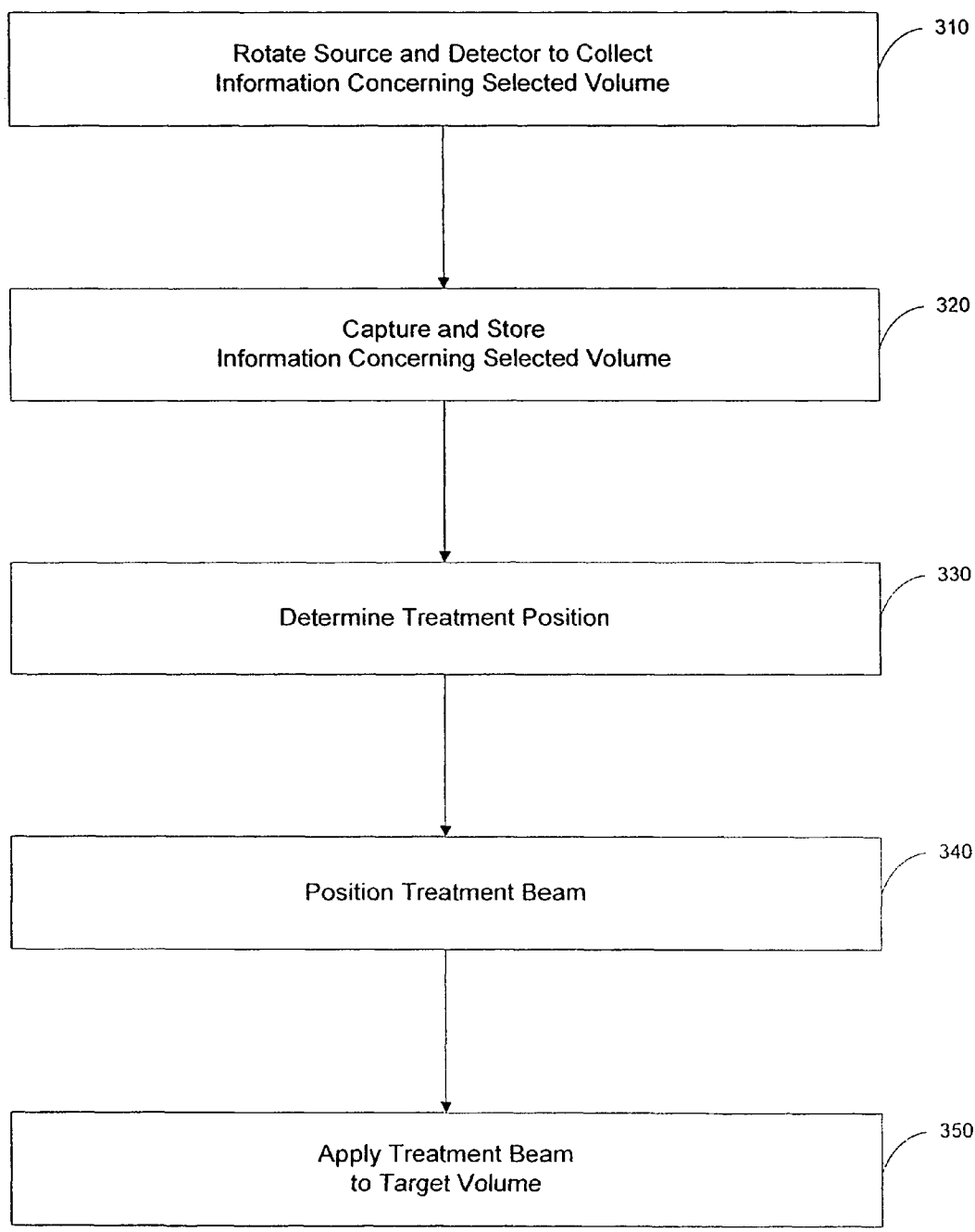
FIG. 4 is a flowchart of an example of an imaging and treatment procedure that may be used with the machine of FIGS. 3A-3C.

FIG. 4 is a flowchart of an example of a method of using the machine 200 to image and provide treatment. At block 310, the source 204 and the detector 206 are both rotated with respect to a patient to image a selected volume, by the gantry 202 and the arms 205, 207. Information concerning a selected volume, such as the shape, size, and location of a tumor in the patient, or the position of an anatomical landmark or other marker, is collected. At block 320, the information concerning the selected volume is captured by the detector 206 and stored, for example, in a computer 165. An image may be generated. Based on the information concerning the selected volume, one or more appropriate treatment positions for the machine 200 may be determined to apply a radiation treatment beam to a target volume, at block 330. The gantry 202 maneuvers the treatment source 212 to the treatment position at block 340 and the treatment beam is applied at the correct dosage to the target volume, at block 350.

The imaging radiation source 204 and detector 206 may be operated either in a continuous or pulsed manner to provide a real time or quasi-real time fluoroscopic image of moving internal anatomy and/or to track the motion of anatomy being treated (due to normal respiration or unwanted voluntary or involuntary patient movement, for example. Each arm 205, 207 may have one or more of either or both of sources 204 and/or image detectors 206, to reduce backscattering where imaging takes place during treatment. Stereoscopic images may also be generated by suitable positioning of multiple sources 204 and/or detectors 206 on the arms 205, 207, and in other manners. These imaging techniques are discussed in more detail in the '167 Publication, which is incorporated by reference herein.

As discussed above, data generated by a detector (or detectors), such as the detector 206 or the detector 214, that is rotated around a target, may cause uniform and non-uniform ring artifacts, such as circular ring artifacts (full or partial), elliptical artifacts and/or variable intensity ring artifacts (referred to collectively as "ring artifacts") to appear in an output image. Therefore, in accordance with an embodiment of the invention, the computer 165 analyzes the image data generated by the image detector 206 to identify any ring artifacts therein, and processes the image data to mitigate the ring artifacts.

Figure 5:
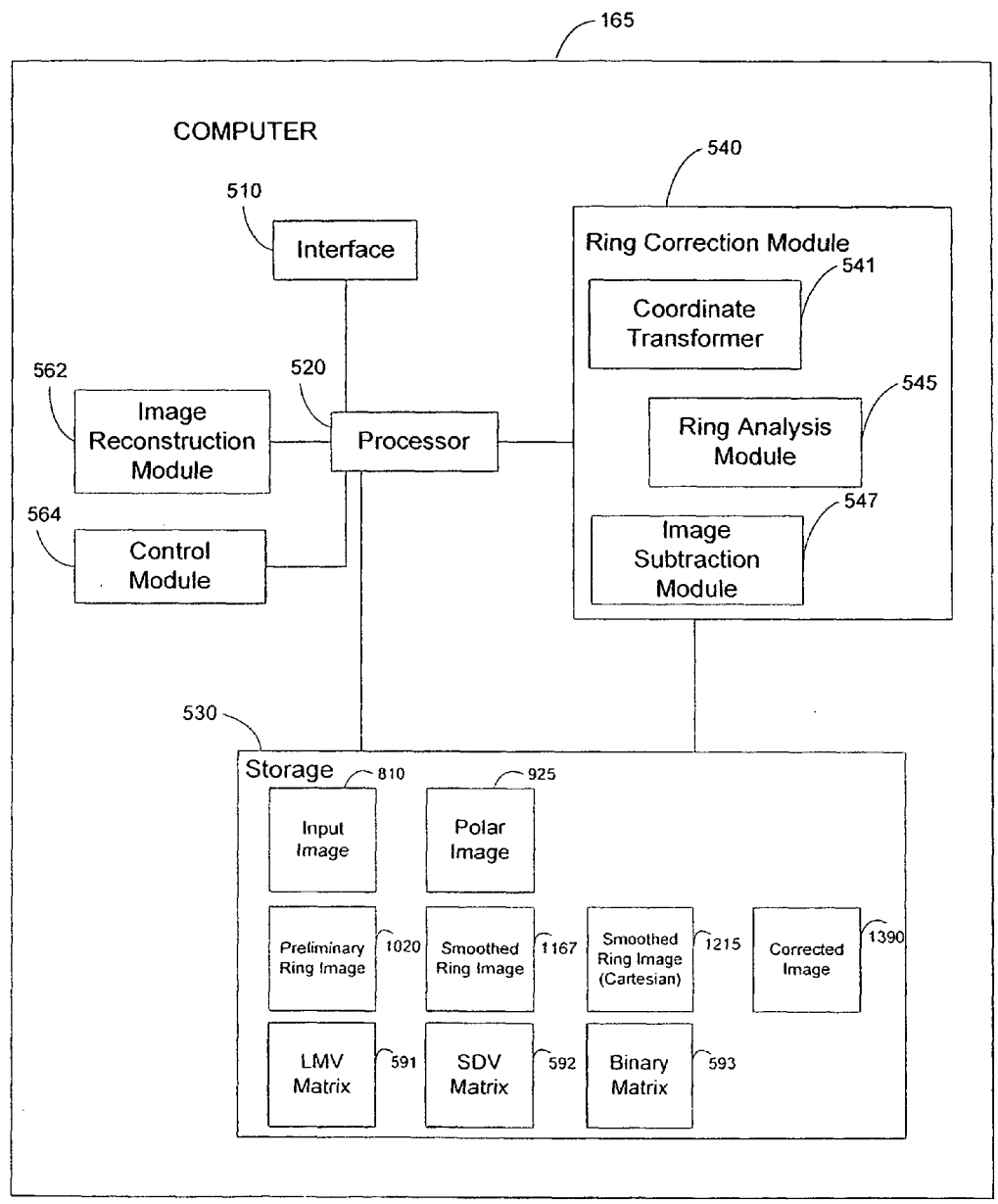
FIG. 5 is a block diagram of an example of components of a computer used to analyze data and correct for ring artifacts, in accordance with an embodiment of the invention.

FIG. 5 is a block diagram of an example of components of the computer 165, in accordance with an embodiment of the invention. The computer 165 comprises an interface 510, a processor 520, and a storage 530. The computer 165 also comprises an image reconstruction module 562, a control module 564, and a ring correction module 540. In the example of FIG. 3, the ring correction module 540 comprises several sub-modules, including a coordinate transformer 541, a ring analysis module 545, and an image subtraction module 547.

The processor 520 orchestrates the activities of the various components of the computer 165. In one example, the processor 520 comprises a central processing unit ("CPU") controlled by software. Alternatively, the processor 520 may comprise specialized circuitry.

The interface 510 provides a communication gateway through which data may be exchanged between the processor 520 and the radiotherapy clinical treatment machine 200. The interface 510 may comprise any one or more of a number of different mechanisms, including, without limitation, one or more SCSI cards, enterprise systems connection cards, fiber channel interfaces, modems, network interfaces, or a network hub.

The storage 530 is used by the processor 520, and by other components of the computer 165 to store data. For example, various data files, including files containing image data, may be stored in the storage 530. In the example of FIG. 3, the storage 530 may comprise one or more disk drives, for example, or may comprise random-access memory (RAM). In alternative examples, the storage 530 may comprise any type of device capable of storing data files, including, without limitation, one or more magnetic tape drives, optical disks, etc.

The control module 564 controls selected functions of the radiotherapy clinical treatment machine 200. For example, the control module 564 may rotate and translate the above devices 202, 204, 206, 212, and 214, to position a target volume in line with the treatment beam that is shaped to the target volume. The control module 364 may comprise software, circuitry, or a combination of software and circuitry.

The image reconstruction module 562 receives raw data resulting from the CT scanning of the selected volume, as generated by the imaging detector 206 and/or the detector 214, and reconstructs the selected volume into an image based on the data. The reconstruction generated by the image reconstruction module 562 is expressed in Cartesian coordinates. The image reconstruction module 562 may comprise software, circuitry, or a combination of software and circuitry. If the radiation is collimated into a cone beam, the image reconstruction module 562 may use a cone-beam back-projection algorithm to reconstruct the data into an image, for example.

The ring correction module 540 analyzes and processes image data. More specifically, after the image reconstruction module 562 generates an input image based on data provided by the imaging detectors 206, 214, the ring correction module 540 examines the input image, identifies ring artifacts therein and mitigates the artifacts. The ring correction module 540 may comprise software, circuitry, or a combination of software and circuitry. As discussed above, the ring correction module 540 comprises several sub-modules, including a coordinate transformer 541, a ring analysis module 545, and an image subtraction module 547.

In accordance with embodiments of the invention, the coordinate transformer 541 transforms image data represented in a first coordinate system into a representation of the image data in a second coordinate system. For example, the coordinate transformer 541 may transform an image expressed in Cartesian coordinates into an image expressed in polar coordinates. A Cartesian coordinate system is a coordinate system in n dimensions where n is any integer made by using n axes which intersect each other at right angles at an origin . . . " McGraw-Hill Dictionary of Scientific and Technical Terms, McGraw-Hill, Sixth Edition, p. 336. In a polar coordinate system, a point in a plane is represented by coordinates $(r, \Theta)$, where $\Theta$ is the angle between the positive x-axis and the ray from the origin to the point, and r is the length of the ray. (Id. at p. 1,628).

The ring analysis module 545 analyzes and processes image data. For example, the ring analysis module 545 may apply various filters to image data to eliminate noise, to smooth the image, etc. The image subtraction module 547 subtracts a first image from a second image, on a pixel-by-pixel basis. The operation of these modules in embodiments of the present invention is discussed further below.

Figure 6:
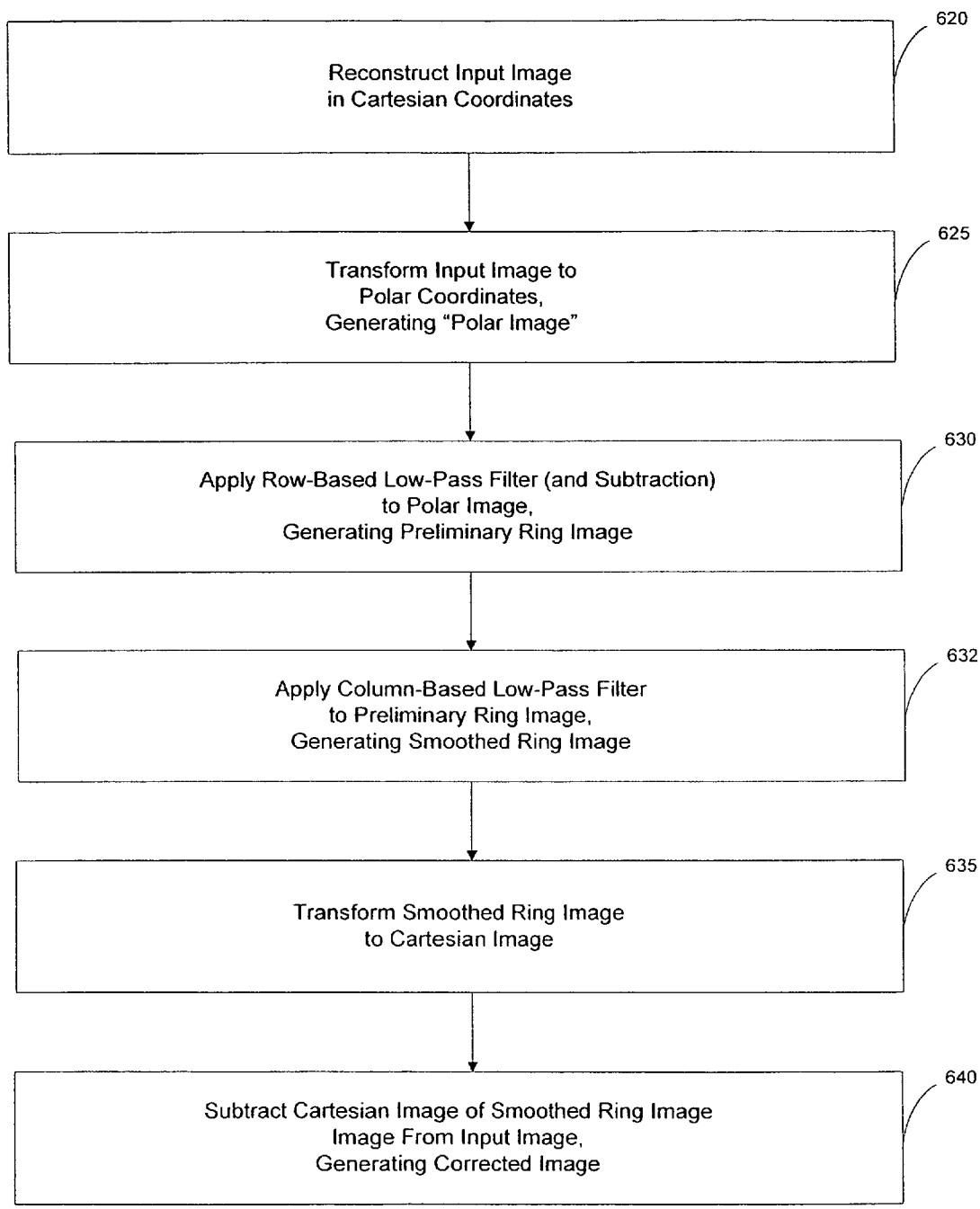
FIG. 6 is a flowchart of an example of a method to identify and mitigate ring artifacts in an image, in accordance with an embodiment of the invention.

FIG. 6 is a flowchart of an example of a method to identify and mitigate ring artifacts in an image, in accordance with an embodiment of the invention. As mentioned above, data obtained from a scanned volume is received from one or more detector(s). In the example of FIGS. 3A-3C and FIG. 5, the processor 520 receives, via the interface 510, digital image data from the detector 206 and/or from the detector 214.

Figure 2:
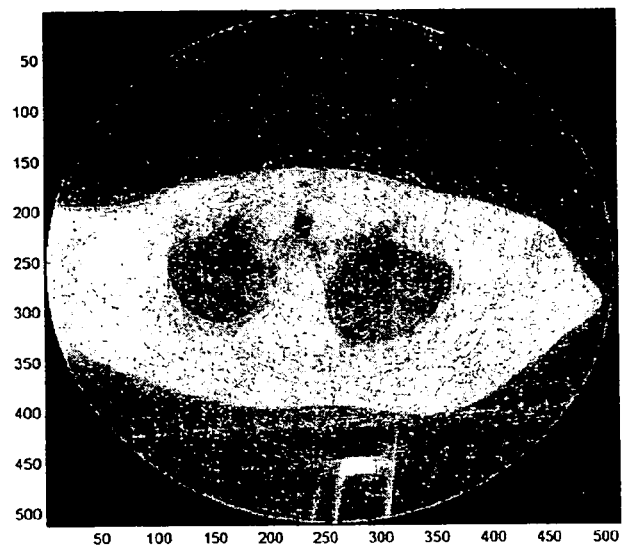
FIG. 2 is an example of an image with ring artifacts.

At Step 620, an input image is reconstructed. In this example, the image reconstruction module 562 receives data from the detectors 206, 214 and generates an input image. The input image comprises a representation, in Cartesian coordinates, of the selected scanned volume. In one example, an input image may comprise an axial representation of a scanned volume. FIG. 2, discussed above, is an example of an input image in Cartesian coordinates.

Figure 7:
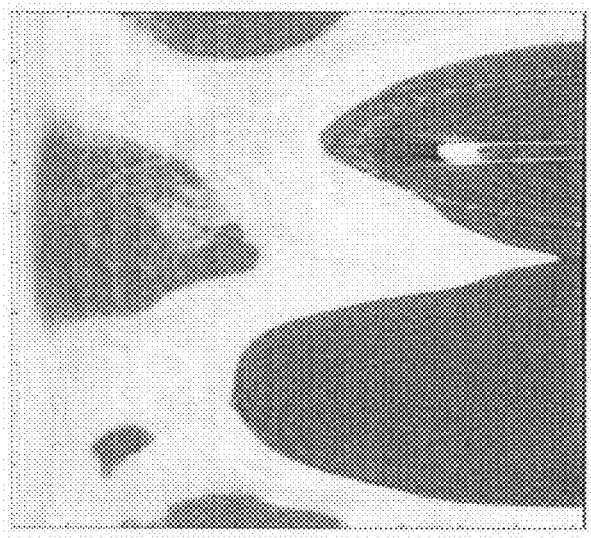
FIG. 7 is an example of a polar image generated based on the image of FIG. 2, in accordance with an embodiment of the invention.

At Step 625, the Cartesian image is transformed into polar coordinates. Thus, coordinate transformer 541 transforms the image into a representation of the scanned volume expressed in polar coordinates. This representation is referred to as the polar image. To generate the polar image, the center of the ring artifacts in the input image is used as the origin. The coordinate transformer 541 may use pre-computed look-up tables to facilitate rapid execution. FIG. 7 is an example of the image of FIG. 2, converted into polar coordinates. In the polar image, the horizontal axis represents radial distance from the origin. The vertical axis represents angle theta ($\Theta$). Therefore, each horizontal row contains pixels associated with a respective angular position and each vertical column contains pixels located at a constant distance from the origin. Spatial resolution resulting from the transformations may be improved by performing sufficiently high order interpolations. Bicubic interpolations and/or bilinear interpolations may be performed, for example, as is known in the art. In addition, it is possible to oversample the polar image radially, as is also known in the art. The polar image may be oversampled by a factor of 1.5, for example. The polar image is stored in the memory 530, as shown in FIG. 5.

Figure 8:
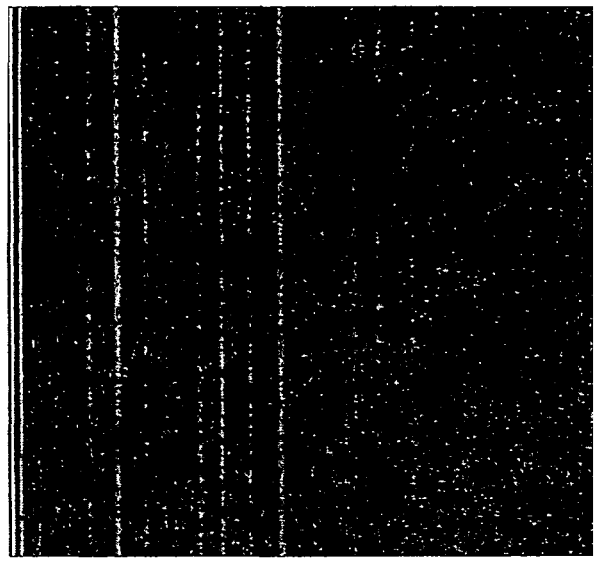
FIG. 8 is a preliminary ring image generated in accordance with an embodiment of the invention.

At Step 630, a row-based low-pass filter is applied to the polar image to generate a preliminary estimate of ring intensities within the image data. In one example, the ring analysis module 545 applies a low-pass filter radially to the polar image and subtracts the filtered image from the polar image, to generate a preliminary ring image containing an estimate of ring artifacts within the input image. An example of a low-pass filter that may be used to perform Step 630 is discussed in more detail below. FIG. 8 is an example of the polar image of FIG. 7 after low-pass filtering.

Figure 9:
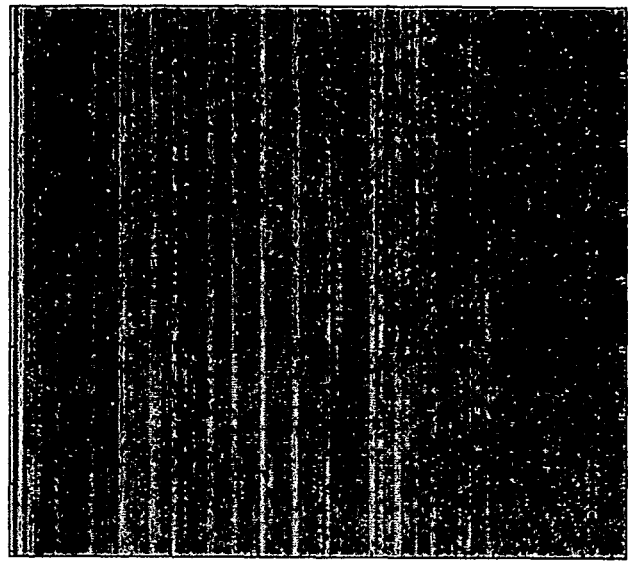
FIG. 9 is a smoothed ring image generated in accordance with an embodiment of the invention.

At Step 632, a column-based low-pass filter is applied to the preliminary ring image to smooth the image. In the example, the ring analysis module 545 applies a column-based low-pass filter (in $\Theta$) to the preliminary ring image, generating a smoothed ring image. FIG. 9 is an example of a smoothed ring image generated in this manner based on the image of FIG. 8.

Figure 10:
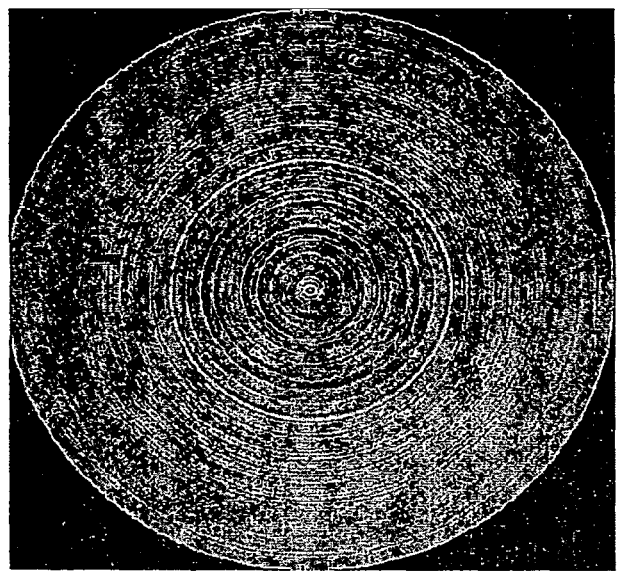
FIG. 10 is a Cartesian version of the smoothed ring image of FIG. 9, generated in accordance with an embodiment of the invention.

The smoothed ring image is transformed to Cartesian coordinates to form a Cartesian image, at Step 635. Thus, the coordinate transformer 541 transforms the smoothed ring image, which is expressed in polar coordinates, to a Cartesian image. FIG. 10 is an example of a Cartesian image resulting from transformation of the smoothed ring image of FIG. 9.

Figure 11:
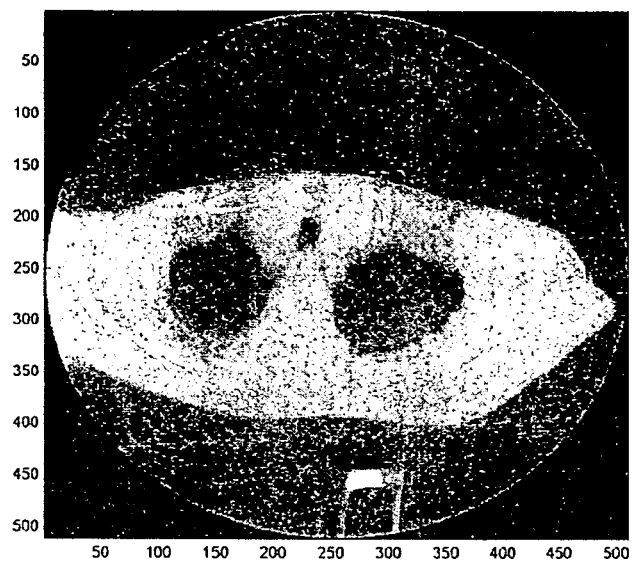
FIG. 11 is a corrected image generated in accordance with an embodiment of the invention.

At Step 640, the Cartesian image of the smoothed ring estimate is subtracted from the original input image. Thus, the image subtraction module 547 subtracts the Cartesian version of the smoothed ring image from the input image, generating a corrected image, an example of which is shown in FIG. 11. Alternatively, the smoothed ring image of FIG. 9 may be subtracted from the polar image of FIG. 7 and the resulting corrected polar image may then be converted to Cartesian coordinates. However, it has also been observed that if the transformation to Cartesian coordinates is performed prior to the subtraction, the transformation can be preformed at a lower resolution than if it is done after the subtraction. A transformation performed at a lower resolution requires fewer resources.

Figure 12:
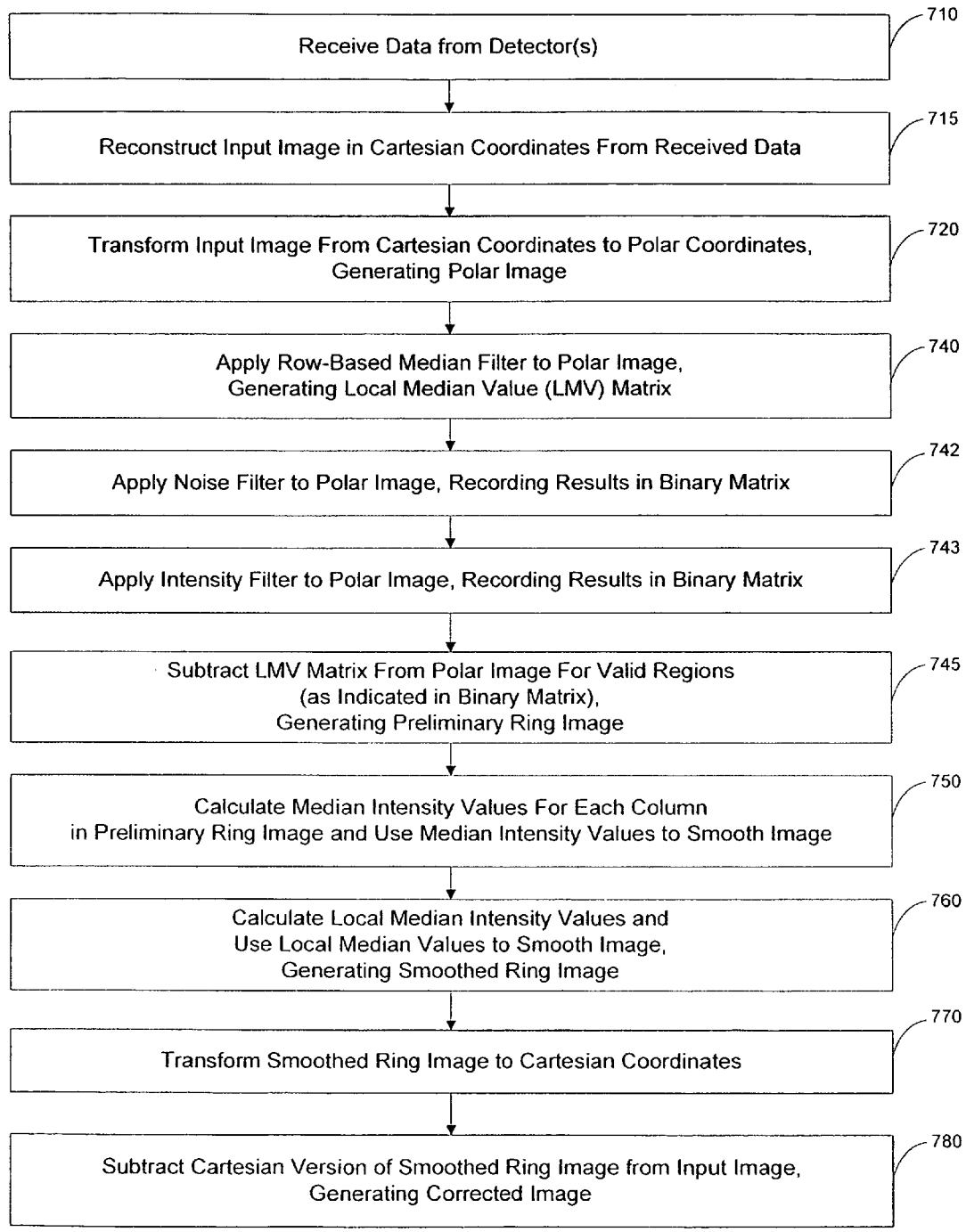
FIG. 12 is a flowchart of another example of a method to mitigate ring artifacts in an image, in accordance with another example of this embodiment.

Additional steps may be added to the method described above to enhance the results. FIG. 12 is a flowchart of another example of a method to mitigate ring artifacts in an image, in accordance with another example of this embodiment. At Step 710, data obtained from a selected volume is received from one or more detector(s), at Step 715, an image is reconstructed in Cartesian coordinates from the received data, and at Step 720, the image is transformed from Cartesian to polar coordinates, as above. As discussed above, FIG. 2 is an example of an input image in Cartesian coordinates. FIG. 7 is an example of a polar image generated based on the image of FIG. 2. Steps 715 and 720 correspond respectively to steps 620 and 625 of FIG. 6.

To generate an estimate of ring artifacts, only low-noise regions of the image that are relatively smooth in the radial direction and devoid of anatomical transitions (such as bone-tissue transitions), may be used. Thus, the polar image is analyzed and processed to remove pixels in areas of the image with a relatively high level of noise. To perform this filtering operation, in one example, the ring analysis module 545 analyzes the polar image and computes a noise-based figure-of-merit for each pixel in the polar image. The noise-based figure-of-merit is computed based on standard deviation values and local median values, and is used to identify pixels associated with high-noise regions. These computations are described below. It should also be noted that steps 740-745 of FIG. 12 describe an example of a low-pass filter that may be used to perform step 630 (of FIG. 6).

First, local median values are computed. At step 740, the ring analysis module 545 applies a row-based median filter to the polar image, generating a local median value matrix ("LMV matrix"). The row-based median filter may be performed using a sliding window technique to compute a local median value for each pixel in each row of the polar image. A window of a predetermined width W is shifted across a row one pixel at a time. The width W of the window, in pixels, is preferably an odd number of pixels, such that at each position, a pixel in the center of the window may be identified and a local median value may be computed for the central pixel. A histogram may be generated at each position and used to determine a local median value, for example. The local median values are stored in a LMV matrix 591, which is stored in the memory 530, as shown in FIG. 5.

The beginning and end of each row of pixels of the polar image are filtered, in one example, by increasing the window width W gradually as the column number increases. Thus, the width W may be set at a minimum value and gradually increase as the window slides across a row until, at a pixel at or near the center of the row, the window width reaches a maximum value. The window width W may remain constant for several pixels, and then decrease until the final pixel is reached.

In an alternative example, an improved estimate of ring intensities near the origin may be obtained by starting the local median filter before the origin in polar space at a "negative" radius. Thus, for a given angle $\Theta$, the median filter begins at the angle $\Theta$-pi at a radius W/2 where W is the width of the median filter window.

While using the sliding window to compute local median values, the ring analysis module 545 may also compute a standard deviation value for each pixel in the polar image. The standard deviation value for the central pixel is computed based on the intensity values of the pixels within the window. In this example, the standard deviation values are stored in an standard deviation value matrix ("SDV matrix") 592, which may also be stored in the memory 530.

At Step 742, a noise filter is applied to the polar image. The ring analysis module 545 identifies pixels in the polar image for which the ratio of the standard deviation value to the local median value (the "SDV-to-LMV ratio") exceeds a predetermined limit. Pixels having an unacceptable SDV-to-LMV ratio are assumed to be associated with an anatomical transition and/or high noise region, and are not subsequently used to estimate ring artifacts. In one example, the predetermined limit for the SDV-to-LMV ratio is 0.1.

The results of the noise filter may be stored in a binary matrix. In this example, the ring analysis module 545 initiates a binary matrix having the same number of pixels and the same dimensions as the polar image, and determines the values of the pixels therein in the following manner. For each pixel in the polar image having an unacceptable SDV-to-LMV ratio, the corresponding pixel in the binary matrix is set to zero. All other pixels in the binary matrix are set to one. Referring to FIG. 5, the ring analysis module 545 stores a binary matrix 593 generated in this manner in the memory 530.

At Step 743, an intensity filter is also applied to the polar image to identify pixels having intensity values outside of a predetermined range. It is useful to identify pixels associated with soft tissue for use in the subsequent estimation of ring artifacts, and, in contrast, remove from consideration pixels associated with air or bone. In this example, the ring analysis module 545 analyzes the data in the polar image and identifies any pixel having an intensity value below a predetermined minimum value or above a predetermined maximum value. In one examples, the predetermined minimum and maximum values are selected based on known intensity values for bone, air, etc. An intensity range of from −500 HU to +500 HU may be used as an estimate of representative soft tissue density, for example.

The results of the intensity filter are recorded in the binary matrix. For each pixel in the polar image having a value outside the predetermined range of the intensity filter, the corresponding pixel in the binary matrix 593 is set to zero. These pixels will not be used to estimate ring intensities. Separately, a list of pixels that fail the noise filter (of Step 742) and the intensity filter (of Step 743) is maintained. This list of pixels will be subsequently used to process the initial estimate of ring artifacts, as discussed below.

The ring analysis module 545 performs an additional filter by examining each column of the polar image to eliminate from consideration columns that do not have a sufficient number of non-zero pixels. If the number of non-zero pixels in a column is less than a predetermined limit, the column is removed from consideration. Accordingly, corresponding pixels in the binary matrix 593 are set to zero.

Regions for which a valid estimate of ring artifacts are now identified, and an image containing a preliminary estimate of ring artifacts is generated. At Step 745, a preliminary ring image is generated by subtracting the LMV matrix from the polar image, in regions that are valid as indicated in the binary matrix 593. Referring to FIG. 5, the image subtraction module 547 examines the binary matrix 593, the LMV matrix 591, and the polar image, and generates a preliminary ring image. The preliminary ring image is generated by subtracting the corresponding pixel value in the LMV matrix 591 from the corresponding pixel value in the polar image, for each non-zero pixel in the binary matrix 593. Pixels having a zero value in the binary matrix 593 are not considered and thus are set to zero in the preliminary ring image. As discussed above, FIG. 8 shows a preliminary ring image generated in this manner, based on the polar image of FIG. 7, the LMV matrix 591 and the binary matrix 593, in accordance with an embodiment of the invention. The preliminary ring image is stored in the memory 530, as shown in FIG. 5.

At Step 750, median intensity values are calculated for each column in the preliminary ring image and used to smooth the image. The ring analysis module 454 calculates the median intensity value for each column in the preliminary ring image. The binary matrix 593 is also examined to determine if the number of non-zero pixels in each respective column exceeds a predetermined limit. If not, the column is deemed not to have any meaningful information relating to ring artifacts. Thus, if the number of non-zero pixels in a column of the binary matrix 593 is insufficient, the column is removed from consideration and no estimate of ring intensities is made for that respective column. The median intensity value for such columns is set equal to zero. The median intensity values for the columns are be stored in a one-dimensional array.

The median intensity values are used to smooth the preliminary ring image. The ring analysis module 545 examines the list of pixels that failed the noise filter (of Step 742 above) or the intensity filter (of Step 743); for each such pixel, the corresponding pixel in the preliminary ring image is set equal to the median ring intensity value of its respective column.

At Step 760, local median intensity values are calculated and used to further smooth the preliminary ring image. The ring analysis module 545 partitions each column of the preliminary ring image into a predetermined number of equally-spaced partitions and computes a local median value of each partition. Each column may be divided into six partitions, for example. The ring analysis module 545 compares the intensity value of each pixel in the preliminary ring image to the applicable local median value. If the pixel's value differs from the applicable local median value by more than a predetermined amount, the pixel's value is changed to be equal to the applicable local median value. The predetermined amount may be selected using a calibration technique, for example. The predetermined amount may be 80 HU, for example.

The ring analysis module 545 may also smooth the columns in the preliminary ring image by circular convolution along $\Theta$ using a uniform window. The length of the window determined as a function of radius. In one example, the convolution angle is set at a high value near the origin, and reduced as radius increases. Alternatively, the columns of the preliminary ring image may be smoothed by applying a median filter to the image data along $\Theta$.

As discussed above, FIG. 9 shows a smoothed ring image generated by applying the aforementioned smoothing techniques to the preliminary ring image of FIG. 8. The smoothed ring image is stored in the memory 530, as shown in FIG. 5.

At Step 770, the smoothed ring image is transformed to Cartesian coordinates. In the example, the coordinate transformer 541 transforms the smoothed ring image to Cartesian coordinates. As discussed above, FIG. 10 shows a Cartesian version of the smoothed ring image of FIG. 9. The Cartesian version of the smoothed ring image is stored in the memory 530, as shown in FIG. 5. Step 770 corresponds to step 635 of FIG. 6.

At Step 780, the Cartesian version of the smoothed ring image is subtracted from the original input image, generating a corrected image. Accordingly, the image subtraction module 547 subtracts the Cartesian version of the smoothed ring image from the input image. As discussed above, FIG. 11 shows a corrected image generated in this manner based on the input image and the Cartesian version of the smoothed ring image shown in FIG. 10, in accordance with an embodiment of the invention. The corrected image is stored in the memory 530, as in FIG. 5. Step 780 corresponds to step 640 of FIG. 6.

While the artifacts shown in FIG. 2 and discussed above have been complete, circular rings, embodiments of the invention described herein may be used to correct for non-uniform artifacts, as well. For example, images containing variable intensity ring artifacts, whose intensity varies as a function of angle, may also be corrected by the processes described above. Embodiments of the invention may also be used to correct for partial ring artifacts, which are generally radial in nature but form only a portion of a ring and elliptical artifacts, which may be full or partial ellipses.

Figure 13A:
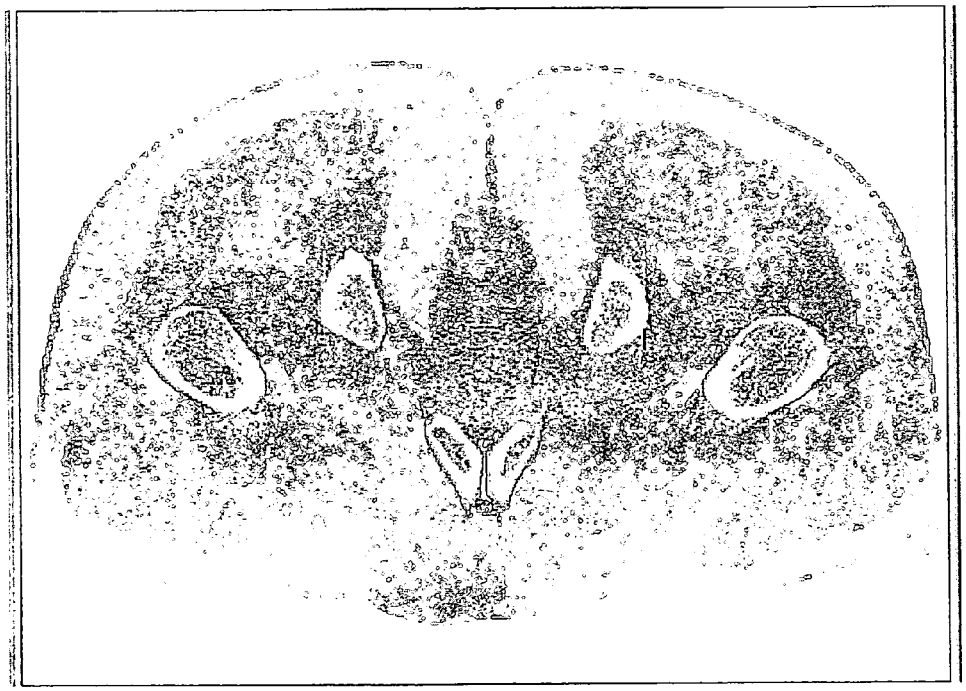
FIG. 13A is an example of an image containing partial ring artifacts, which may also be corrected in accordance with an embodiment of the invention.
Figure 13B:
FIG. 13B is a corrected image based on the image of FIG. 13A, generated in accordance with an embodiment of the invention.

FIG. 13A shows an example of an image containing partial ring artifacts. FIG. 13B shows an example of a corrected image generated based on the image of FIG. 13A, in accordance with this embodiment of the invention. To obtain the corrected image of FIG. 13B, the partial ring artifacts apparent in the image of FIG. 13A were mitigated using the methods described herein, taking into consideration that a partial ring artifact will appear in only part of a column, in polar coordinates.

When analyzing elliptical ring artifacts in accordance with the methods described herein, the ring artifacts may appear as partial ring artifacts in two or more adjacent columns, in the polar image. Alternatively, a modified polar coordinate system may be used to express individual elliptical artifacts within single columns. Such a modified polar coordinate system is considered to be a polar coordinate system, for purposes of this application.

In one example of an embodiment of the invention, methods described herein may be implemented in the form of computer-readable software, for example, and stored on a suitable storage medium, such as a floppy disk, a hard disk, a compact disk (CD), an optical disk, etc. For example, the image reconstruction module 562, the control module 564, and the ring correction module 540 may be implemented in the form of software and stored on a compact disk. In one example, methods described herein may be implemented as computer-readable code generated using the c/C++.

Figure 14:
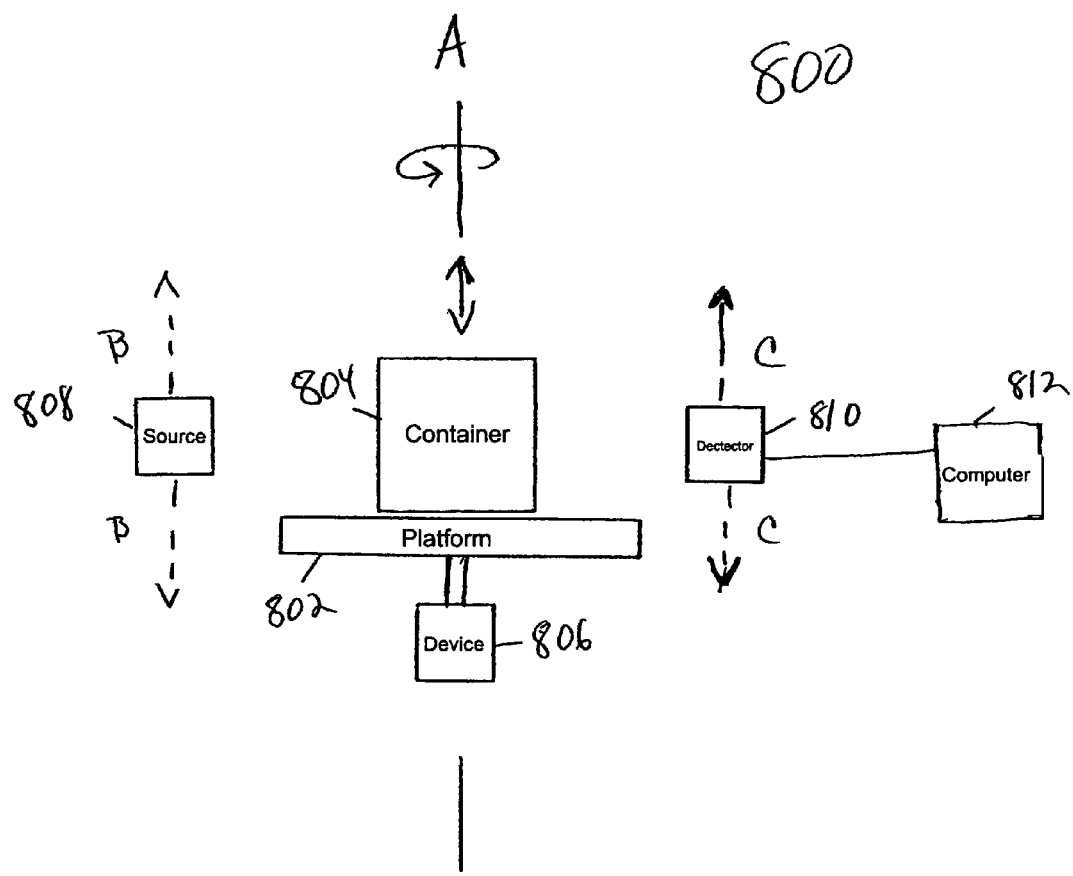
FIG. 14 is a schematic representation of a CT system wherein a target is rotated during scanning, which can also result in ring artifacts.

As mentioned above, ring artifacts may also appear in images resulting from CT scanning of a rotating target. FIG. 14 is a schematic representation of an example of a CT system 800 comprising a rotatable platform 802, which in this example supports a rectangular container 804 and rotates the container around an axis A. The platform is rotatable by a device 806, to enable scanning at a sufficient number of angles for CT reconstruction, as is known in the art. A source 808 and a detector 810 are also shown. The source 808 may emit a fan beam or a cone beam of radiation, such as X-ray radiation, for example, towards the container 824. After transmission through the container 804, the radiation is detected by a detector 810. The detector 810 provides an output to a computer 812 for reconstruction and ring correction, as above.

In one example, the platform 802 is also vertically displaceable to enable scanning of different vertical planes of the container. Examples of devices 806 that may be used to provide rotation and vertical displacement of the platform 802 include a screw jack or a motor supported by a pneumatic or hydraulic lift. The platform 802 may be rotated clockwise or counterclockwise, and may be raised or lowered continuously or incrementally during scanning or incrementally between scans. In that case, the source 808 and the detector 810 may be stationary. Optionally, the source 808, the detector 810, and the rotating platform 802 may all be movable vertically.

In another example, the platform 802 is only rotatable, such as by a motor device 806, and the source 808 and/or detector 810 may be moved up and down to enable scanning in multiple vertical planes, as indicated by phantom arrows B, C which are parallel to the direction of the axis A.

Scanning systems, including CT scanning systems, with rotatable platforms and rotatable/vertically displaceable platforms are described in more detail in U.S. application Ser. No. 10/310,060, which was filed on Dec. 4, 2002, was published on Jun. 10, 2004 bearing Publication Number 2004/0109532, is assigned to the assignee of the present invention, and is incorporated by reference herein.

It should be noted that the computer 165 of FIG. 3A and FIG. 5 is disclosed herein in a form in which various functions are performed by discrete functional blocks. However, any one or more of these functions could equally well be embodied in an arrangement in which the functions of any one or more of those blocks or indeed, all of the functions thereof, are realized, for example, by one or more appropriately programmed processors.

The foregoing merely illustrates the principles of the invention. It will thus be appreciated that those skilled in the art will be able to devise numerous other arrangements which embody the spirit and scope of the invention, which is defined by the following claims.

We claim:

1. A method to correct for ring artifacts in an image, comprising:
    reconstructing a first Cartesian image based on data received from an imaging device, in Cartesian coordinates;
    transforming the first Cartesian image into a first polar image in polar coordinates;
    applying a first low-pass filter to the first polar image, in a radial dimension, to form a second polar image;
    subtracting the second polar image from the first polar image to form a third polar image;
    applying a second low-pass filter to the third polar image, in an angular dimension, to form a fourth polar image;
    transforming the fourth polar image to Cartesian coordinates to form a second Cartesian image; and
    correcting the first Cartesian image based, at least in part, on the second Cartesian image.

2. The method of claim 1, wherein the first Cartesian image is corrected by:
    subtracting the second Cartesian image from the first Cartesian image.

3. The method of claim 1, wherein applying the first low-pass filter comprises:
    applying a median filter in the radial dimension.

4. The method of claim 3, wherein applying the median filter comprises:
    determining local median values with a sliding window technique in the radial dimension.

5. The method of claim 3, comprising:
    determining local median values by use of a histogram.

6. The method of claim 1, wherein applying the second low-pass filter comprises:
    calculating median intensity values for sets of pixels at constant angular values; and
    replacing selected values in the third polar image with median intensity values.

7. The method of claim 6, wherein applying the second low-pass filter further comprises:
    applying circular convolution in an angular dimension.

8. The method of claim 1, wherein applying the first low-pass filter comprises:
    applying one or more selected filters to identify one or more regions in the first polar image in which a valid estimate of ring artifacts can be obtained; and
    subtracting the second polar image from the first polar image only in the one or more identified regions to form the third polar image.

9. The method of claim 8, wherein the one or more selected filters comprise a noise filter.

10. The method of claim 9, wherein the one or more selected filters further comprises an intensity filter.

11. The method of claim 8, wherein the one or more selected filters comprise an intensity filter.

12. The method of claim 8, further comprising:
recording the one or more regions in a binary matrix.

13. The method of claim 1, comprising:
transforming the first Cartesian image into the first polar image by use of pre-computed look-up tables.

14. The method of claim 1, wherein the ring artifacts are from the group consisting of circular artifacts, elliptical artifacts, partial ring artifacts, and variable intensity artifacts.

15. A method to correct for ring artifacts in an image comprising:
converting a first Cartesian image in Cartesian coordinates into a first polar image in polar coordinates;
identifying polar ring artifacts in the first polar image;
filtering the identified polar ring artifacts to generate a second, uncorrected polar image; and
obtaining a corrected Cartesian image based, at least in part, on the second, uncorrected polar image.

16. The method of claim 15, wherein obtaining the corrected Cartesian image comprises:
converting the second, uncorrected polar image into a second Cartesian image; and
subtracting the second Cartesian image from the first Cartesian image.

17. The method of claim 15, wherein identifying polar ring artifacts comprises:
applying a first low-pass filter to the first polar image, in a radial dimension, to form a low-pass filtered polar image; and
subtracting the low-pass filtered polar image from the first polar image to generate a polar ring artifact image.

18. The method of claim 17, wherein filtering the polar ring artifacts comprises:
applying a second low-pass filter to the polar ring artifact image, in an angular dimension, to form the second, uncorrected polar image.

19. The method of claim 18, wherein obtaining the first corrected Cartesian image comprises:
converting the second, uncorrected polar image to Cartesian coordinates to form a second Cartesian image; and
subtracting the second Cartesian image from the first Cartesian image.

20. The method of claim 15, wherein the ring artifacts are from the group consisting of circular artifacts, elliptical artifacts, partial ring artifacts, and variable intensity artifacts.

21. A computed tomography system comprising:
a support to support a target;
at least one radiation source positioned to irradiate the target;
at least one detector positioned to detect radiation interacting with the target; and
a processor coupled to the detector, the processor configured to correct for ring artifacts by:
converting a Cartesian image in Cartesian coordinates into a polar image in polar coordinates;
identifying polar ring artifacts in the first polar image;
filtering the identified polar ring artifacts to generate a second, uncorrected polar image; and
obtaining a corrected Cartesian image based, at least in part, on the second uncorrected polar image.

22. The system of claim 21, further comprising:
a second support rotatable around an axis;
wherein:
at least one of the at least one sources is coupled to the second support;
at least one of the at least one detectors is coupled to the second support; and
the support is configured to rotate the source and the detector around the axis, to scan the target, during operation.

23. The system of claim 22, wherein:
the second support comprises a rotatable gantry.

24. The system of claim 23, wherein:
the at least one source and the at least one detector are coupled to the gantry.

25. The system of claim 24, wherein the support further comprises:
wherein the at least one of the at least one source is coupled to the first arm and the at least one of the at least one detector is coupled to the second arm.

26. The system of claim 21, wherein the support is rotatable to rotate the target around an axis; and
at least one of the at least one source, the at least one detector, or the support is movable along a direction parallel to the axis.

27. The system of claim 26, wherein the support is movable vertically.

28. The system of claim 26, wherein the at least one source and the at least one detector are movable vertically.

29. The system of claim 21, further comprising:
a radiotherapy system.

30. A method of conducting computed tomography, comprising:
irradiating a target;
detecting radiation interacting with the target;
reconstructing an image in Cartesian coordinates based, at least in part, on radiation detected by the detector;
converting the image in Cartesian coordinates into polar coordinates to form a first polar image;
identifying polar ring artifacts in the first polar image;
filtering the identified ring artifacts in polar coordinates to form a second, uncorrected polar image; and
obtaining a corrected Cartesian image based, at least in part, on the second uncorrected polar image.

31. The method of claim 30, further comprising:
rotating at least one radiation source and at least one detector around the target.

32. The method of claim 30, further comprising:
rotating the target around an axis; and
moving at least one radiation source, at least one detector, and/or the rotating target along a direction parallel to the axis.

33. The method of claim 30, further comprising:
converting the filtered polar ring artifacts into Cartesian ring artifacts; and
subtracting the Cartesian ring artifacts from the Cartesian image.

34. The method of claim 30, wherein the ring artifacts are in the group consisting of circular artifacts, elliptical artifacts, partial ring artifacts, and variable intensity artifacts.

35. A system to correct for ring artifacts in an image, comprising:
a memory to store data;
a processor coupled to the memory, the processor being configured to:
convert a Cartesian image in Cartesian coordinates into a first polar image in polar coordinates;
identify polar ring artifacts in the first polar image;
filter the identified polar ring artifacts to generate a second, uncorrected polar image; and obtain a corrected Cartesian image based, at least in part, on the second, uncorrected polar image.

36. The system of claim 35, wherein the processor is configured to identify polar ring artifacts by:
applying a first low-pass filter to the first polar image; and
subtracting the resulting low-pass filtered image from the first polar image, to generate a polar ring artifact image.

37. The system of claim 36, wherein the processor is configured to:
apply the first low-pass filter by applying a median filter to a first, uncorrected polar image in a radial dimension.

38. The system of claim 37, wherein the processor is configured to:
apply the median filter by use of a sliding window technique to determine local median values.

39. The system of claim 37, wherein the processor is configured to filter the identified polar ring artifacts by:
applying a second low-pass filter to the polar ring artifact image in an angular dimension.

40. The system of claim 35, wherein the processor is configured to identify polar ring artifacts in the first polar image by:
applying one or more selected filters to identify one or more regions in the first polar image in which a valid estimate of ring artifacts can be obtained;
applying a first low-pass filter to the first polar image, in a radial dimension; and
subtract the resulting low-pass filtered image from the first polar image to generate the polar ring artifact image only in the one or more identified regions.

41. The system of claim 40, wherein the one or more selected filters comprise a noise filter.

42. The system of claim 41, wherein the one or more selected filters further comprise an intensity filter.

43. The system of claim 40, wherein the one or more selected filters comprise an intensity filter.

44. The system of claim 40, wherein the processor is further configured to:
record the one or more regions in a binary matrix.

45. The system of claim 35, wherein the processor is configured to:
transform the Cartesian image into the first polar image by use of one or more pre-computed look-up tables.

46. The system of claim 35, wherein the ring artifacts are in the group consisting of circular, elliptical, partial artifacts, and variable intensity artifacts.

47. A non-transitory computer readable medium storing computer readable code for use in an image processing system to correct for ring artifacts in an image, the code comprising instructions to:
convert a Cartesian image into a first polar image;
identify polar ring artifacts in the first polar image;
filter the identified polar ring artifacts to generate a second, uncorrected polar image; and
obtain a corrected Cartesian image based, at least in part, on the second uncorrected polar image.

48. The computer readable medium of claim 47, wherein the code comprises instructions to:
identify the polar ring artifacts in the first polar image by applying a first low-pass filter to the first polar image to form a polar ring artifact image.

49. The computer readable medium of claim 48, wherein the code comprises instructions to:
apply the first low-pass filter by applying a median filter to the first polar image in a radial dimension.

50. The computer readable medium of claim 49, wherein the code comprises instructions to:
apply the median filter by use of a sliding window technique to determine local median values.

51. The computer readable medium of claim 49, wherein the code comprises instructions to:
apply the median filter by use of a histogram.

52. The computer readable medium of claim 48, wherein the code comprises instructions to:
filter the identified polar ring artifacts by applying a second low-pass filter to the polar ring artifact image.

53. The computer readable medium of claim 52, wherein the code comprises instructions to:
apply the second low-pass filter to the polar ring artifacts by calculating median intensity values for sets of pixels in the polar ring artifact image at constant angular values; and
replacing values of selected pixels in the polar ring artifact image with median intensity values.

54. The computer readable medium of claim 53, wherein the code further comprises instructions to:
apply circular convolution to the polar ring artifacts in an angular dimension.

55. The computer readable medium of claim 48, wherein the code further comprises instructions to:
apply one or more selected filters to identify one or more regions in the first polar image in which a valid estimate of ring artifacts can be obtained;
and
subtract the filtered image from the first polar image to generate the polar ring artifact image only in the one or more identified regions.

* * * * *